(12) United States Patent
Kondo et al.

(10) Patent No.: US 6,653,119 B1
(45) Date of Patent: Nov. 25, 2003

(54) WHITE ROT FUNGI AND METHOD FOR DECOMPOSING DIOXINS USING THEM

(75) Inventors: Ryuichiro Kondo, 1-23-8-408, Kashii, Higashi-ku, Fukuoka-shi, Fukuoka 813-0011 (JP); Kokki Sakai, Fukuoka (JP); Koichi Wakao, Fukuoka (JP)

(73) Assignees: Bio Remediation Technologie, Inc. (JP); Ryuichiro Kondo (JP)

( * ) Notice: Subject to any disclaimer, the term of this patent is extended or adjusted under 35 U.S.C. 154(b) by 58 days.

(21) Appl. No.: 09/805,127

(22) Filed: Mar. 14, 2001

Related U.S. Application Data

(63) Continuation-in-part of application No. 09/786,683, filed on Mar. 8, 2001, now abandoned, which is a continuation-in-part of application No. PCT/JP99/04744, filed on Sep. 1, 1999.

(30) Foreign Application Priority Data

Sep. 14, 1998 (JP) .......................................... 10-260707

(51) Int. Cl.⁷ .............................. B09B 3/00; C12N 1/14; C12N 1/16; C02F 1/00; A62D 3/00
(52) U.S. Cl. ..................................... 435/262.5; 588/205
(58) Field of Search ........................ 435/262.5; 588/205

(56) References Cited

U.S. PATENT DOCUMENTS 5,486,474 A * 1/1996 Bradley et al. .............. 435/262
6,063,979 A * 5/2000 Miyata et al. .............. 588/205

OTHER PUBLICATIONS

Ryuichiro Kondo et al "Degradation of Dioxins and PCBs by Using White Rot Fungus" Abstract 64th Conference on Paper Pulp Research Jun. 1997 pp. 32–44.*

Kondo R. et al, *Degradation of Polychlorinated Dioxins and Polychlorinated Biphenys by White Rot Fungi,*, The 64th Conference on Paper Pulp Research, (1997),32–355.

Takada, S., et al., *Applied and Environmental Microbiology*, 62(12): 4323–4328 (1998).

Takada, S., *Bio Industry*, 14(10): 5–12 (1997).

Takada, S., *Kagaku(Chemistry)*, 52(10): 24–25 (1997).

* cited by examiner

*Primary Examiner*—Herbert J. Lilling
(74) *Attorney, Agent, or Firm*—Shanks & Herbert

(57) ABSTRACT

White rot fungi capable of decomposing dioxin were screened from rotten wood to isolate the MZ-340 strain. This MZ-340 could be cultured in the Kirk liquid medium (HCLN) or PDB medium. New systems that can be used to decompose dioxins in incineration ash were constructed using this MZ-340 strain. The present invention can decompose dioxins in incineration ash effectively and efficiently in both solid phase systems and liquid phase systems. Thus, the present invention enables the prevention of environmental pollution by dioxins generated during incineration and also the clean up of dioxin pollutants.

7 Claims, 8 Drawing Sheets

SEQUENCE LISTING

```
<160> NUMBER OF SEQ ID NOS: 7

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 1
tgtagtcata tgcttgtctc aa                                              22

<210> SEQ ID NO 2
<211> LENGTH: 20
<212> TYPE: DNA
```

```
<213> ORGANISM: Artificial Sequence
<220> FEATURE:
<223> OTHER INFORMATION: Description of Artificial Sequence:
      artificially synthesized sequence

<400> SEQUENCE: 2
atacgctatt ggagctggaa                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 3
tcccagctcc aatagcgtat                                                    20

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 4
cctggtggtg cccttcc                                                       17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 5
ggaagggcac caccagg                                                       17

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 6
tcctctaaat gaccaagttt g                                                  21

<210> SEQ ID NO 7
<211> LENGTH: 1665
<212> TYPE: DNA
<213> ORGANISM: White rod fungus MZ-340

<400> SEQUENCE: 7
atgtccaagt ataaacaaat ttgtactgtg aaactgcgaa tggctcatta aatcagttat        60
agtttatttg atggtgcttt gctacatgga taactgtggt aattctagag ctaatacatg       120
caatcaagcc ccgacttctg gaagggtgt atttattaga taaaaaacca atgcggttcg       180
ccgctccctt ggtgattcat aataacttct cgaatcgcat ggccttgtgc cggcgatgct       240
tcattcaaat atctgcccta tcaactttcg atggtaggat agaggcctac catggtttca       300
```

-continued

```
acgggtaacg gggaataagg gttcgattcc ggagagggag cctgagaaac ggctaccaca      360
tccaaggaag gcagcaggcg cgcaaattac ccaatcccga cacggggagg tagtgacaat      420
aaataacgat atagggctct tttgggtctt ataattggaa tgagtacaat ttaaatctct      480
taacgaggaa caattggagg gcaagtctgg tgccagcagc cgcggtaatt ccagctccaa      540
tagcgtatat taaagttgtt gcagttaaaa agctcgtagt tgaacttcag acctggctgg      600
gcggtccgcc taacggtgtg tactgtctgg ctgggtctta cctcttggtg agccggtatg      660
cccttcactg ggtgtatcgg ggaaccagga cttttacctt gagaaaatta gagtgttcaa      720
agcaggcctg cgcctgaata cattagcatg gaataataaa ataggacgtg cggttctatt      780
ttgttggttt ctagagtcgc cgtaatgatt aatagggata gttgggggca ttagtattcc      840
gttgctagag gtgaaattct tggatttacg gaagactaac tactgcgaaa gcatttgcca      900
aggatgtttt cattaatcaa gaacgaaggt taggggatcg aaaacgatca gataccgttg      960
tagtcttaac agtaaactat gccgactagg gatcggcgga actcaatttg atgtgtcgct     1020
cggcacctta cgagaaatca aagtctttgg gttctggggg gagtatggtc gcaaggctga     1080
aacttaaagg aattgacgga agggcaccac caggtgtgga gcctgcggct taatttgact     1140
caacacgggg aaactcacca ggtccagaca tgactaggat tgacagattg atagctcttt     1200
catgatttta tgggtggtgg tgcatggccg ttcttagttg gtggagtgat ttgtctggtt     1260
aattccgata acgaacgaga ccttaacctg ctaaatagcc tggccggctt ttgctggtca     1320
ctggcttctt agagggactg tctgcgtcta gcagacggaa gtttgaggca ataacaggtc     1380
tgtgatgccc ttagatgttc tgggccgcac gcgcgctaca ctgacagagc cagcgagttt     1440
ttttccttgg ccggaaggtc tgggtaatct tgtgaaactc tgtcgtgctg gggatagagc     1500
attgcaatta ttgctcttca acgaggaata cctagtaagc gtgagtcatc agctcgcgtt     1560
gattacgtcc ctgccctttg tacacaccgc ccgtcgctac taccgattga atggcttagt     1620
gaggtcttga gattggcgac agggagccgg caacggcacc ctgtt                    1665
```

WHITE ROT FUNGI AND METHOD FOR DECOMPOSING DIOXINS USING THEM

This application is a continuation-in-part of U.S. application Ser. No. 09/786,683, filed Mar. 8, 2001, now abandoned and a continuation-in-part of PCT Application No. JP99/04744, filed Sep. 1, 1999, published in Japanese.

TECHNICAL FIELD

The present invention relates to white rot fungi having the activity of efficiently decomposing dioxins, as well as a method for decomposing dioxins by using the white rot fungi. In more detail, the present invention relates to a method for decomposing dioxins in incineration ash by using white rot fungi and crude extracellular enzymes from the white rot fungi.

BACKGROUND ART

It has been said that dioxins are the most hazardous poison generated by human activities ever. It has strong toxicity resulting in carcinogenesis, weight loss, thymus atrophy, skin disorders, hepatic disorders, teratogenicity, etc. Because the compounds are chemically stable, there are also environmental concerns about their accumulation. The environmental dispersion of dioxins generated during waste incineration has become a serious problem worldwide. Dioxins are grouped into several categories based on their chemical structures. There are 70 or more known isomers of polychlorinated dibenzo-p-dioxins (PCDDs). This category contains 2,3,7, 8-tetrachlorodibenzo-p-dioxin (2,3,7, 8-$T_4$CDD), which is known to be highly toxic. 2,3,7,8-$T_4$CDD shows extremely high acute toxicity, having a $LD_{50}$ value of 0.6 to 2.0 $\mu$g/kg for guinea pigs. Other dioxins are also known, which include polychlorinated dibenzofurans (PCDFs) and coplanar polychlorinated biphenyls (Co-PCBs), both having several isomers.

Dioxins are generated mainly by incineration. The source includes nonindustrial waste incineration, industrial waste incineration, metal refining, petroleum additives (lubricating oil), cigarette smoke, recycled black-liquor boilers, incineration of wood and discarded material, auto emissions, etc. Dioxins are also generated in the bleaching process of bleached kraft-pulp production, in the process of manufacturing agricultural chemicals such as PCNB, and such processes. Among them, the incineration of non-industrial waste is estimated to generate about 80% of the total dioxin output. For example, more than 4000 gTEQ of dioxin is produced annually in Japan due to non-industrial waste incineration.

Industrially advanced nations are already taking measures to legally regulate dioxin release by restricting the dioxin concentration released from incinerators. Even in the mechanical aspect, the combustion efficiency of incinerators, and the treatment of released gases have been improved, producing effective results. However, dioxins already released into the environment have polluted the soil, and leachates have been polluted by fly ash and also by incineration ash buried at final disposal sites. These dioxin pollutions are serious problems and dioxin-decomposing countermeasures should be taken immediately.

In recent years, bioremediation is gaining the spotlight as a means for eliminating pollutants that have been released into the environment. Bioremediation is a technology by which environmental pollutants are processed using microbial functions, finally converting pollutants into non-toxic substances such as carbonic acid gas, water, inorganic salt, and such. Bioremediation is further divided into biostimulation and bioargumentation. The former is the means of enhancing the functional activity of microorganisms present in the polluted environment by adding nutrient salts, improving aeration, etc. The latter is the means of introducing microorganisms having a cleaning function into the polluted environment.

Microbial decomposition of dioxin is divided into three classes depending on the type of microorganism or enzyme used, namely, (1) aerobic decomposition by bacteria, (2) reductive dechlorination by anaerobes, and (3) decomposition by Basidiomycetes.

Only a few research reports exist regarding the decomposition by bacteria. Recently, a series of evaluations were done on the genus Sphingomonas. Wittich et al. screened strains capable of growing in the presence of dibenzo-p-dioxin (DD) and dibenzofuran (DF) as a unique carbon source and succeeded in the isolation of the Sphingomonas sp. RW1 strain (Wittich, R. et al., Appl. Environ. Microbiol., 1992, 58, 1005–1010; H. -A. Arfmann et al., Appl. Environ. Microbiol., 1997, 63, 3458–3462) and HH69 strain (Harms, H. et al., Appl. Environ. Microbiol., 1995, 61, 2499–2505). RW1 strain was capable of decomposing chloro- and dichloro-substituted dioxins, but could not decompose further-substituted dioxins. The decomposition products obtained were salicylic acid, catechol, and chlorinated compounds thereof (Wilkes, H. et al., Appl. Environ. Microbiol., 1996, 62, 367–371). In addition to these studies, there are reports on the decomposition of dioxins such as dibenzofuran and dibenzo-p-dioxin by utilizing aerobic bacteria such as the genus Pseudomonas and the genus Alcaligenes (G. Schreiner et al., Chemosphere, 1997, 34, 1315–1331). There are also some reports on dioxin decomposition by anaerobic microorganisms (P. Adriaens etal., Environ. Sci. Technol., 1995, 29, 2252–2260; J. E. M. Beurskensetal., Environ. Toxicol. Chem., 1995, 14, 939–943). For example, these include the dechlorination of heptachlorodibenzo-p-dioxin (HpCDD) to hexachlorodibenzo-p-dioxin (HxCDD) as well as the conversion from 1,2,3,4-tetrachlorodibenzo-p-dioxin (1,2,3,4-TCDD) to dichlorodibenzo-p-dioxin (2-CDD) by anaerobic microorganisms within sludge (Wittich, R. et al., Appl. Microbiol. Biotechnol., 1998, 49, 489–499). However, there are concerns of more toxic compounds being generated during the decomposition processes. In addition to these microorganisms, others capable of decomposing dioxins have been identified (Hammer et al., Appl. Environ. Microbiol., 1998, 64, 2215–2219).

Bumpus et al. have suggested that a white rot fungus, *Phanerochaete chrysosporium*, which belongs to Basidiomycetes, might be capable of decomposing several types of persistent substances (Bumpus, J. A. et al., Science, 1985, 228, 1434–1436). Since the publication of this report, many researchers have been interested in the decomposition of environmental pollutants by white rot fungi, and thus, there are many reports concerning this matter. However, reports on decomposition of dioxins are small in number. Valli et al. found that the decomposition was markedly enhanced when 2,7-dichlorodibenzo-p-dioxin (2,7-DCDD) was treated with *P. chrysosporium* in a medium having a poor nitrogen source. Based on this finding, the authors deduced that the lignin-decomposing enzyme system participates in dioxin decomposition (Valli, K. et al., J. Bacteriol., 1992, 174, 2131–2137). DD was further treated with lignin peroxidase (LiP), obtaining an ether-linkage cleavage product (Joshi, D. et al., Biochem., 1994, 33, 10969–10976). However, it is questionable that LiP would act on a compound having more than two chloro-substitutions.

The present inventors have previously reported that the YK-624 strain of the white rot fungus *Phanerochaete sordida* is capable of decomposing dioxins such as polychlorinated dibenzodioxins (PCDDs) and polychlorinated dibenzofurans (PCDFs) (Takada, S. et al., Appl. Environ. Microbiol., 1996, 62, 4323–4328). It is known that white rot fungi are capable of decomposing various environmental pollutants such as chlorophenol, chloroaniline, PCBs, a variety of agricultural chemicals, aromatic hydrocarbon compounds, nitro compounds, dyes, and so on in addition to dioxins. Accordingly, attention is being given to the fungus as a useful and key organism for environmental cleanup. However, in order to practically use the method of white rot fungus-mediated dioxin decomposition, it is necessary to discover a white rot fungus strain having a high dioxin-decomposing activity. Such strains should further be able to decompose not only particular types of dioxins, but also a variety of dioxins contained in incineration ash, etc. Even when the activity of decomposing dioxin is recognized in a test tube, it is necessary to construct new systems for decomposing dioxins present in wastes such as incineration ash, etc. Thus, when it comes to the practical use of dioxin decomposition by white rot fungi, many problems remain to be solved.

DISCLOSURE OF THE INVENTION

β-ether linkage comprises about 50% of total chemical bonds present in lignin. Therefore, enzymes having ether linkage-cleaving activity may play important roles in the decomposition of lignin. The present inventors thought that dioxins could effectively be decomposed by using white rot fungi exhibiting a high lignin-decomposing activity. Based on this idea, the inventors screened white rot fungi, which had been isolated from natural sources, for fungi capable of decomposing 2,7-dichlorodibenzo-p-dioxin (2,7-DCDD) and succeeded in isolating the white rot fungus strain MZ-340 that exhibited a particularly high lignin-decomposing activity within the Kirk liquid medium (HCLN). The strain white rot fungus MZ-340 could efficiently be cultured in the Kirk liquid medium (HCLN) or potato dextrose (PDB) medium. Further, the inventors prepared a crude extracellular enzyme solution from the culture supernatant of MZ-340 strain, and incubated it with 2,7-dichlorodibenzo-p-dioxin (2,7-DCDD). The result showed that 2,7-DCDD had been decomposed by the strain.

The white rot fungus strain MZ-340 grew well in a medium containing incineration ash and exhibited hypha extension. Therefore, a system was constructed for the decomposition of dioxins in incineration ash by using this MZ-340 strain. MZ-340 was cultured in various media containing 2,7-DCDD, and decreases in the amount of 2,7-DCDD were evaluated. While a low rate of decrease was observed in the potato dextrose (PDB) medium and HCHN medium having a rich nitrogen source, the rate of decrease in the amount of 2,7-DCDD was markedly high in the HCLN medium having a poor nitrogen source. Next, the white rot fungus strain MZ-340 was cultured in the Kirk liquid medium (HCLN), and then incineration ash was added thereto for the decomposition of dioxins. The result showed that various dioxins contained in incineration ash were efficiently decomposed by about a 2 to 4 week culture. Further, the present inventors cultured the white rot fungus in a large scale using a wood-based material, and mixed the cultured fungus with incineration ash. Thus the inventors succeeded in the construction of a solid-phase system for decomposing dioxins in incineration ash. Namely, a system for decomposing dioxins contained in incineration ash using the white rot fungus was constructed by the present invention for the first time.

In other words, an objective of the present invention is to provide the white rot fungus strain MZ-340 that has the activity of decomposing dioxins. Due to using the strain MZ-340, the present invention is highly advantageous by having a very high dioxin-decomposing ability as never before achieved with conventional white rot fungi. It is also advantageous that the white rot fungus MZ-340 can be cultured in a large scale in the Kirk liquid medium (HCLN) or potato dextrose medium (PDB). It is also possible to culture MZ-340 in a large scale by using a wood-based material at a low cost.

Another objective of the present invention is to provide a method of decomposing dioxins by utilizing the white rot fungus MZ-340. The inventive method for decomposing dioxins is expected to be widely applicable in various fields.

Yet another objective of the present invention in more specific embodiments is to provide a method for decomposing dioxins by contacting dioxins with the strain MZ-340, crude extracellular enzyme from MZ-340, a medium containing MZ-340, or a culture medium of MZ-340 that does not substantially contain fungal bodies of MZ-340.

By utilizing the white rot fungus MZ-340, it is possible to decompose various dioxins including polychlorinated dibenzo-p-dioxin and polychlorinated dibenzofuran.

Still another objective of the present invention is to provide a method for decomposing dioxins present in incineration ash using white rot fungi other than the white rot fungus MZ-340. In one of the embodiments, the present invention provides a liquid-phase method for decomposing dioxins by using the Kirk liquid medium (HCLN), and such. In another embodiment, the present invention provides a method for decomposing dioxins by mixing incineration ash with white rot fungi in a solid phase.

Specifically, the present invention relates to white rot fungi capable of decomposing dioxins and a method of decomposing dioxins using white rot fungi, and more specifically relates to:

(1) a method for decomposing a dioxin in incineration ash, the method comprising incubating a mixture of:
   (a) a white rot fungus, a crude extracellular enzyme from a white rot fungus, a medium containing a white rot fungus, or a culture medium of a white rot fungus that does not substantially contain fungal bodies of the white rot fungus, and
   (b) incineration ash;

(2) the method of (1), wherein the mixture is incubated in a liquid phase;

(3) the method of (2), wherein the mixture is incubated in the Kirk liquid medium (HCLN);

(4) the method of (1), wherein the mixture is incubated in a solid phase;

(5) the method of (4), wherein the mixture is incubated in the presence of a wood-based material;

(6) the method of (1), wherein the white rot fungus is specified by the accession number FERM BP-6864;

(7) a white rot fungus specified by the accession number FERM BP-6864;

(8) a method for decomposing a dioxin, the method comprising contacting a dioxin with a white rot fungus specified by the accession number FERM BP-6864, a crude extracellular enzyme from the white rot fungus, a medium containing the white rot fungus, or a culture medium of the white rot fungus that does not substantially contain fungal bodies of the white rot fungus; and (9) the method of (8), wherein the dioxin is polychlorinated dibenzo-p-dioxin or polychlorinated dibenzofuran.

The present invention provides the white rot fungus MZ-340 capable of decomposing dioxins. The inventive white rot fungus MZ-340 has been deposited in the following depositary authority.

(a) Name and address of depositary authority
 Name: National Institute of Bioscience and Human-Technology, Advanced Industrial Science and Technology, Ministry of Economy, Trade and Industry
 Address: (Zip code 305-8566)
 1-1-3 Higashi, Tsukuba, Ibaraki, Japan (b) Date of deposition (Date of original deposition): Sep. 7th, 1998

(c) Accession number: FERM BP-6864

The white rot fungus MZ-340 grows well in the PDA medium (potato extract 200 g/l, glucose 20 g/l, and agar 15 g/l) under aerobic conditions at 300° C., forming a thick mycelial colony. It is also possible to liquid-culture the fungus in the Kirk liquid medium (HCLN) or PDB medium. The fungus can be cultured in a large-scale using a wood-based material such as wood chips or wood meal.

The white rot fungus MZ-340 has a high decomposing activity against 2,7-dichlorodibenzo-p-dioxin (2,7-DCDD) and is also capable of decomposing polychlorinated dibenzo-p-dioxins such as tetrachlorodibenzodioxin, pentachlorodibenzodioxin, hexachlorodibenzodioxin, heptachlorodibenzodioxin, and octachlorodibenzodioxin as well as polychlorinated dibenzofurans such as tetrachlorodibenzofuran, pentachlorodibenzofuran, hexachlorodibenzofuran, heptachlorodibenzofuran, and octachlorodibenzofuran. Thus, various dioxins can be decomposed by utilizing the white rot fungus MZ-340.

In the present invention, the term "dioxin" includes mono- or polychlorinated dibenzo-p-dioxin (chlorine atom: 1 to 8) as indicated in formula (I), and mono- or polychlorinated dibenzofuran (chlorine atom: 1 to 8) as indicated in formula (II).

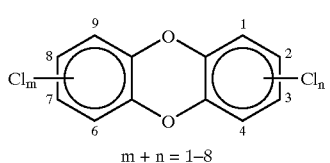

(I)

m + n = 1–8

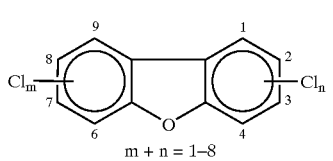

(II)

m + n = 1–8

There are many isomers of these dioxins (Table 1). The white rot fungus MZ-340 of the invention can decompose dioxins including the respective isomers.

TABLE 1

The numbers of isomers of PCDD and PCDF
(substituted compound at position 2, 3, 7, or 8 in parentheses)

| chlorine | PCDD isomers | PCDF isomers |
|---|---|---|
| 1 | 2 | 4 |
| 2 | 10 | 16 |
| 3 | 14 | 28 |
| 4 | 22(1) | 38(1) |
| 4 | 14(1) | 28(2) |
| 4 | 10(3) | 16(4) |
| 4 | 2(1) | 4(2) |
| 4 | 1(1) | 16(1) |
| Total | 75(7) | 135(10) |

The inventive method for decomposing dioxins using white rot fungus MZ-340 comprises contacting dioxins with MZ-340, crude extracellular enzyme from MZ-340, a medium containing MZ-340, or a culture medium of MZ-340 that does not substantially contain fungal bodies of MZ-340. Decomposing dioxins with MZ-340 can be conducted in both liquid and solid phases.

In addition, the present invention provides a method for decomposing dioxins in incineration ash using the white rot fungus MZ-340 or other white rot fungi. The method comprises incubating a mixture of (a) white rot fungi, crude extracellular enzyme from white rot fungus, a medium containing white rot fungi, or a culture medium of white rot fungus that does not substantially contain fungal bodies of white rot fungi, and (b) incineration ash.

There is no particular limitation on white rot fungus to be used for the decomposition, and the white rot fungus MZ-340 strain or a fungus taxonomically related to this strain can be used preferably in the present invention. In the present invention, preferred fungi include, for example, fungi belonging to the order Aphyllophorales, specifically, for example, white rot fungi belonging to the family Corticiaceae (see "Illustrated book of shelf fungi," Ed. Kanagawa Mushroom Society, Chikyusya; The NCBI Taxonomy Homepage, http://www.ncbi.nlm.nih.gov/htbin-post/Taxonomy/wgetorg?mode=Tre e&id=5303&lvl=3&keep=1&srchmode=1&unlock), Coriolaceae (The NCBI Taxonomy Homepage, supra), and Polyporus ("Illustrated book of shelf fungi," Ed. Kanagawa Mushroom Society, Chikyusya). The family Corticiaceae includes fungi having the morphological feature of a fruit body that is spread thinly like a plaster. In a wide sense, the family Corticiaceae includes members that are fully or partially dorsifixed onto wood or bark surface, have flat hymeniums, and are related to fungus group of the family Thelephoraceae in the Fries classification ("Illustrated book of shelf fungi"; The NCBI Taxonomy Homepage, supra).

As listed in the NCBI Taxonomy Homepage, the family Corticiaceae contains, specifically, the genus Acanthophysium, Aleurocystidiellum, Aleurodiscus, Athelia, Basidioradulum, Butlerelfia, Christiansenia, Corticium, Cystostereum, Cytidia, Dendrophora, Dentocorticium, Duportella, Entomocorticium, Hyphoderma, Hyphodontia, Peniophora, Phanerochaete, Phlebia, Pulcherricium, Resinicium, Vuilleminia, and mitosporic Corticiaceae (including Fibularhizoctonia). The family Coriolaceae contains, specifically, the genus Abortiporus, Anomoporia, Antrodia, Antrodiella, Aurantiporus, Auriporia, Bjerkandera, Ceriporia, Ceriporiopsis, Cerrena, Coriolopsis, Coriolus, Cryptoporus, Daedalea, Daedaleopsis, Datronia, Diplomitoporus, Donkioporia, Fomes, Fomitopsis, Gelatoporia, Hapalopilus, Laetiporus, Leptoporus, Megasporoporia, Melanoporia, Meripilus, Nigroporus, Nothopanus, Oligoporus, Ossicaulis, Oxyporus, Perenniporia, Piptoporus, Poria, Postia, Rigidoporus, Tinctoporellus, Trametes, Trichaptum, Tyromyces, Wolfiporia, and unidentified Polyporaceae (including Basidiomycete CECT 20197, and Polyporaceae sp.) (The NCBI Taxonomy Homepage, supra).

In the present invention, white rot fungus to be used for decomposing dioxins in incineration fly ash includes, more preferably, the genus Ceriporia, the genus Phanerochaete, the genus Phlebia, and white rot fungi related to these (for example, the genus Bjerkandera, etc.). Among them, particularly preferred are fungi belonging to the genus Ceriporia. A particularly preferred white rot fungus is the MZ-340 strain (FERM BP-6864).

In one of the embodiments of the present invention for decomposing dioxins in incineration ash, the decomposition is conducted in a liquid phase. For example, dioxins in incineration ash are decomposed when white rot fungi are cultured in a liquid medium mixed with polluted materials containing incineration ash or dioxins derived from incineration ash. There is no particular limitation on the medium, as long as the white rot fungi grow well and dioxins are decomposed. However, media with poor nitrogen sources are preferable for higher dioxin-decomposing activity. For example, such media include the Kirk liquid medium (HCLN) and also a medium containing 20 g/l glucose and 5 g/l Amix (Nippon Pharmaceutical Co.). Culture conditions are exemplified as follows. Namely, the culture is carried out at 20 to 35° C. in a mixture containing the fungus mixed at a 10 to 50% ratio with incineration ash, and glucose is freshly added to the medium at a final concentration of about 1% every week. However, if desired, one skilled in the art can find suitable conditions other than these.

In another embodiment of decomposing dioxins in a liquid phase, dioxins are decomposed by using a crude extracellular enzyme from white rot fungus, a medium containing white rot fungus, or a culture medium of white rot fungus that does not substantially contain fungal bodies of white rot fungi. Since a medium containing white rot fungus or a medium in which white rot fungus was cultured contains crude extracellular enzymes having the activity of decomposing dioxins, dioxins can be decomposed when incineration ash is mixed with such mediums. The crude extracellular enzyme used may be an unpurified enzyme contained in the medium or the purified enzyme.

The liquid-phase method is advantageous as it can highly efficiently decompose dioxins present in incineration ash within a short period of time. Thus, this method is expected to be applied in dioxin-treating plants, and such.

In another embodiment of the present invention for decomposing dioxins in incineration ash, the decomposition is conducted in a solid phase. Such decomposition systems are of much practical use because a large quantity of fungal bodies can be used for the treatment of dioxins in incineration ash. The white rot fungus can be cultured by using wood-based materials such as wood chips or wood meal. Dioxins in incineration ash can be treated with the white rot fungus by mixing a fungus culture medium containing the fungus with incineration ash, and such. The quantity ratio between incineration ash and medium (containing the fungus) is preferably 1:1 to 1:16. It is possible to pre-culture fungal bodies in the culture medium and then mix it with a wood-based material and incineration ash. Dioxins in incineration ash can be decomposed simply by allowing the mixture to stand, for example, at room temperature or in the open.

In the present invention, materials that can be treated includes not only incineration ash, but also soil containing incineration ash, fly ash, solid materials such as filling material used in a washing columns and such, liquids containing dioxins including washing solutions and cooling water, and leachates polluted with dioxins from fly ash and incineration ash buried at final disposal sites, and so on.

BEST MODE FOR CARRYING OUT THE INVENTION

Figure 1:
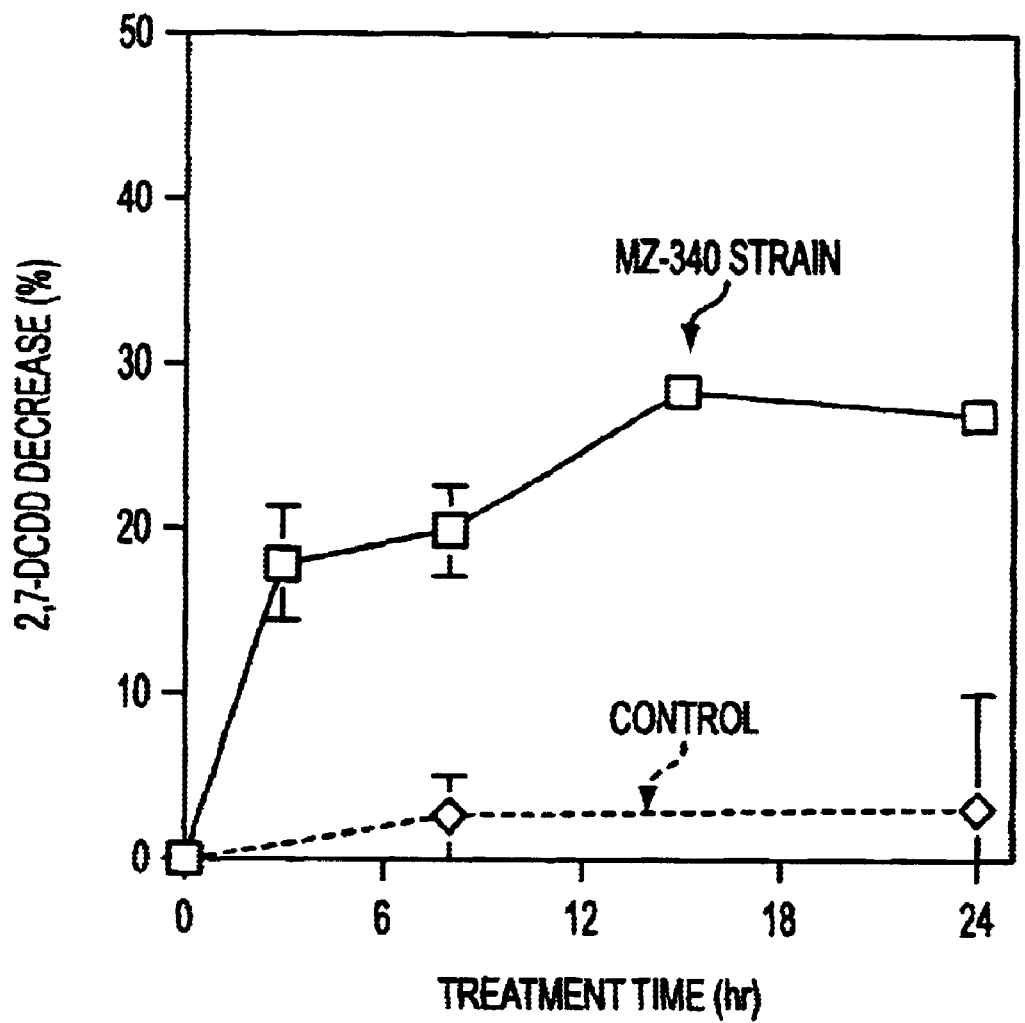
FIG. 1 shows a graph indicating the decomposition of 2,7-dichlorodibenzo-p-dioxin (2,7-DCDD) by the white rot fungus MZ-340.

The present invention is further illustrated in detail below with reference to Examples, but it is not to be construed as being limited thereto. Any patents, patent applications, and publications cited herein are incorporated by reference.

EXAMPLE 1

Screening for White Rot Fungus MZ-340

For screening the white rot fungus, each fungus was grown until it spread on a PDA medium, and 5 fungal discs of about 10-mm diameter were removed from the medium and inoculated into 10 ml of Kirk liquid medium (HCLN) [Methods in Enzymology, vol.161, p.240] or PDB medium (Wako pure chemical industries Co.) contained in 100-ml Erlenmeyer flasks. The pH of each medium was 4.5. Next, a pre-culture was performed at 30° C. for 7 days without shaking. The air in the flasks was replaced with oxygen, and then 2,7-dichlorodibenzo-p-dioxin (2,7-DCDD) (in DMF solution) was added thereto at a final concentration of 25 $\mu$M. The flask was plugged tightly and allowed to stand still for a static culture at 30° C. for 10 days. After the culture, the fungal bodies and the culture solution were homogenized together with ethyl acetate. The resulting ethyl acetate layer was analyzed by GC-MS to determine the recovery rate of the substrate. This screening successfully isolated the white rot fungus strain MZ-340 having the activity of efficiently decomposing 2,7-DCDD with a low substrate recovery rate of 42%. The white rot fungus MZ-340 was originally collected from rotten wood present in a forest belonging to the School of Agriculture, Kyushu University in Miyazaki Prefecture, Japan. The white rot fungus MZ-340 belongs to Basidiomycetes from the standpoint of taxonomy. Its scientific features include the activity of decomposing lignin in wood and good growth in the potato glucose medium forming a thick mycelial colony. This fungal strain has been deposited as "white rot fungus MZ340" in the following depositary authority.

(a) Name and address of depositary authority
   Name: National Institute of Bioscience and Human-Technology, Advanced Industrial Science and Technology, Ministry of Economy, Trade and Industry
   Address: (Zip code 305-8566)
   1-1-3 Higashi, Tsukuba, Ibaraki, Japan
(b) Date of deposition (Date of original deposition): Sep. 7th, 1998
(c) Accession number: FERM BP-6864

EXAMPLE 2

Culture of White Rot Fungus MZ-340

The inventive white rot fungus MZ-340 grew well forming a thick mycelial colony when cultured in the PDA medium composed of 200 g/l potato extract, 20 g/l glucose, and 15 g/l agar under aerobic conditions at 30° C. for 1 week in the dark.

EXAMPLE 3

Treatment of 2,7-DCDD with Crude Extracellular Enzyme

Pre-cultured MZ-340 in PDA medium was homogenized by a Waring blender. The homogenized fungal culture (one fourth of the hyphae spread on a 15 cm-diameter plate) was added to 200 ml of Kirk liquid medium (HCLN) in a 500-ml Erlenmeyer flask. The mixture was then cultured at 30° C. while shaking for 7 days, and oxygen purging was started in the third day of the culture. At the end of culture, the fungal bodies were removed by filtration and the filtrate was further successively filtered with a paper filter, glass-fiber filter, and 3.0- and 0.45-$\mu$m membrane filters. The resulting filtrate obtained was used as an crude extracellular enzyme solution. The reaction system contained 3 ml of 50 mM malonate buffer (pH 4.5) and 2 ml of crude extracellular enzyme solution, and 2,7-DCDD was added thereto at a final concentration of 50 $\mu$M. The reaction was incubated at 30° C. for the time period required. A sample of enzyme inactivated by boiling was used as a control. The buffer alone was added to the reaction in place of the crude extracellular enzyme, and the recovery of 2,7-DCDD was assayed in the same manner. The ratio between this value and the value obtained for a sample containing the enzyme was used to calculate the rate of decrease.

From the result obtained, it was revealed that the crude extracellular enzyme from MZ-340 had the activity of decomposing 2,7-DCDD. The result is shown in FIG. 1. The graph in FIG. 1 shows significant differences between MZ-340 and the control. Further, the crude extracellular enzyme exhibited no lignin peroxidase (Lip) activity and decreases in substrate amounts were not detected in the manganese peroxidase activity (MnP) assay. Each enzyme activity was assayed according to the method as described in a reference "Methods in Enzymology vol.161, P.243 and P.259."

EXAMPLE 4

Culture of White Rot Fungus in a Liquid Medium to which Incineration Ash has been added The MZ-340 strain was grown on a PDA medium plate. Aliquots (20 ml) of a medium containing 2% glucose and 0.5% Amix (Nippon Pharmaceutical Co.) were dispensed into 100-ml Erlenmeyer flasks. 0.2 g of incineration ash (fly ash) was added to each flask and autoclaved. Three pieces of 5 mm×1 mm fungal discs from a plate where fungi were spread, were inoculated into the flasks and the culture was incubated without shaking at 22° C. for 2 weeks. The hyphae grew well in the medium containing fly ash. Fungal bodies were found to grow enwrapping the fly ash.

EXAMPLE 5

Influence of the Type of Medium on the Decrease of Dioxin by White Rot Fungus MZ-340

MZ-340 strain was precultured on a PDA medium plate for 5 days. Aliquots (75 ml) of Kirk basal liquid medium (HCHN or HCLN, pH 4.5) or potato dextrose (PDB) medium (pH 4.5) were dispensed into 200-ml Erlenmeyer flasks with stoppers. The precultured fungal bodies were homogenized in each medium and a 5-ml aliquot of the resulting suspension was added to each flask. The flask was capped with aluminum foil and then cultured at 30° C. while shaking at 130 rpm. In the fifth day of culture, a 50$\mu$l aliquot of 5 mM 2,7-DCDD was added to each flask. The flasks were plugged with stoppers and then cultured at 300° C. with shaking at 130 rpm for 7 days. Control samples were autoclaved at the time when 2,7-DCDD was added. After incubation, 10-ml of concentrated sulfuric acid was added thereto and then anthracene was further added as an internal standard. Then the mixture was extracted with hexan, and the rate of decrease of 2,7-DCDD was assayed by GC/MS.

Figure 2:
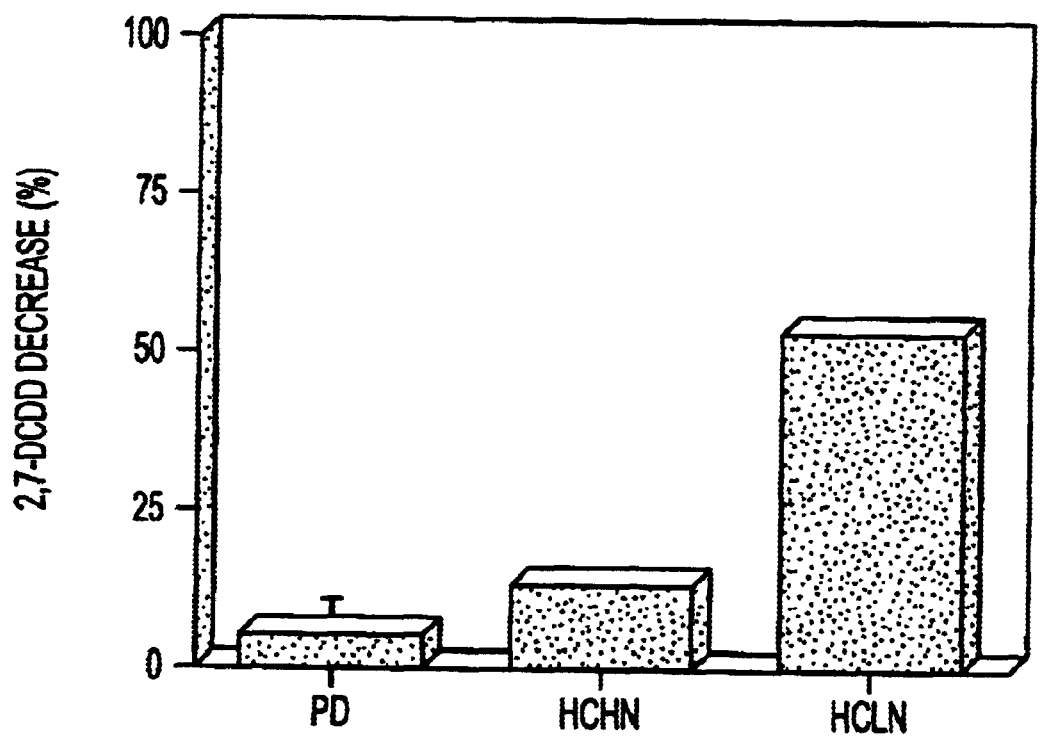
FIG. 2 shows a graph indicating the influence of media on the 2,7-DCDD decomposing activity of white rot fungus MZ-340.

FIG. 2 shows the reduction in the amount of 2,7-DCDD in the above experiment. The reduction rate of 2,7-DCDD was low being about 5% and 10% respectively in the PDB medium and HCHN medium having a rich nitrogen source, but the reduction reached 53% in the HCLN medium. Namely, this suggests that the decomposition is associated with lignin-decomposition related enzymes that are expressed when the nitrogen source was poor.

EXAMPLE 6

Decomposition of Dioxin in Incineration Ash by Using a Liquid Culture System

MZ-340 strain was grown for 5 days until it spread on a PDA medium plate. Aliquots (80 ml) of Kirk liquid medium (HCLN) were added into 200-ml Erlenmeyer flasks with stoppers. Fly ash (1% (w/v) in absolute dry weight) was added to each flask. The pH of the mixture was adjusted to 4.5. The mixture was autoclaved at 121° C. for 20 minutes. A disc of fungi spread on a plate (diameter; 9 cm) and 50 ml Kirk liquid medium (HCLN) were combined together and homogenized by a Waring blender. Aliquots (5 ml) of the homogenate (absolute dry weight; 20 mg) were added to the flasks. The mixtures were cultured at 30° C. while shaking at 130rpm. Autoclaved fungal bodies were added to some flasks as controls and were cultured while shaking in the same manner.

After a 2-week culture, hydrochloric acid was added to the Erlenmeyer flask at a final concentration of 2 N. The flask was allowed to stand still for 2 hours. After hydrolysis with hydrochloric acid, the solution was filtered with a glass-fiber filter, and the resulting residue was air-dried. The residue was extracted with toluene by using the Soxhlet extraction method for 16 hours, and the filtrate was subjected to liquid-liquid shaking extraction with dichloromethane in a shaker, repeating the extraction two times. The respective extracts were combined together, and the internal standard $^{13}C_{12}$-2378-$T_4$CDD/F-$O_8$CDD/F was added thereto. Concentrated sulfuric acid (95%, 10 ml) was added to the mixture. The resulting mixture was shaken for 10 minutes in a shaker, repeating the shaking treatment 3 times. After washing with pure water, the mixture was dehydrated and concentrated with Glauber's salt.

Silica gel (2 g), which had been heated at 120° C. in an oven for 3 hours, was wet-filled into a column. The elution was carried out with 100 ml of n-hexan. Basic alumina (10 g), of which the activity grade is 1, was wet-filled into a column. Pre-elution was carried out with 100 ml of 2% dichloromethane-hexan solvent, and the subsequent elution was performed with 100 ml of 50% dichloromethane-hexan solvent. The sample obtained was concentrated to near dryness, $^{13}C_{12}$-1234-$T_4$CDD and $^{13}C_{12}$-123789-$H_6$CDD were added as internal standards thereto. Toxic equivalents (TEQ) and concentrations of a variety of dioxin isomers were analyzed by HRGC-HRMS.

Each of TCDD, TCDF, PeCDD, PeCDF, HxCDD, and HxCDF was analyzed by using a SP-2331 column (Supelco; inner diameter 0.25 mm×length 60 mm, filter thickness 0.20 µm). The final sample volume was 200 µl and the input sample volume was 1 µl, and the analysis was done at channel 1. Parameters (setting m/z) areas follows: TCDD (321.8936, 319.8965), TCDF (305.8987, 303.9016), PeCDD (355.8546, 357.8517), PeCDF (339.8597, 341.8568), HxCDD (389.8157, 391.8127), HxCDF (373.8207, 375.8175), 37C14-TCDD (327.8847), 13C-TCDD (333.9338), 13C-TCDF (317.9389), 13C-PeCDD (367.8949), 13C-PeCDF (351.9000), 13C-HxCDD (401.8559), and 13C-HxCDF (385.8610); monitoring time was 27 msec, switching time was 45 msec, and switching period was 0.99 sec.

Each of HPCDD, HpCDF, OcCDD, and OcCDF was analyzed by using a DB-5 column (J&W; inner diameter 0.25 mm×length 60 mm, filter thickness 0.25 µm). The final sample volume was 200 µl and the input sample volume was 1 µl; parameters (setting m/z) and channel number are as follows: channel 1:TCDD (321.8936, 319.8965), 13C-TCDD (333.9338, 331.9368), and 37Cl-TCDD (327.8847); monitoring time was 27 msec, switching time was 45 msec, and switching period was 0.32 sec; channel 2:HpCDD (423.7767, 425.7737), HpCDF (407.7818, 409.7788), OcCDD (459.7348, 457.7377), OcCDF (443.7398, 441.7428), 13C-HpCDD (435.8169, 437.8140), 13C-HpCDF (419.8220, 421.8141), 13C-OcCDD (471.7750, 469.7783), and 13C-OcCDF (455.7801, 453.7830); monitoring time was 27 msec, switching time was 45 msec, and switching period was 0.81 sec.

Figure 3:
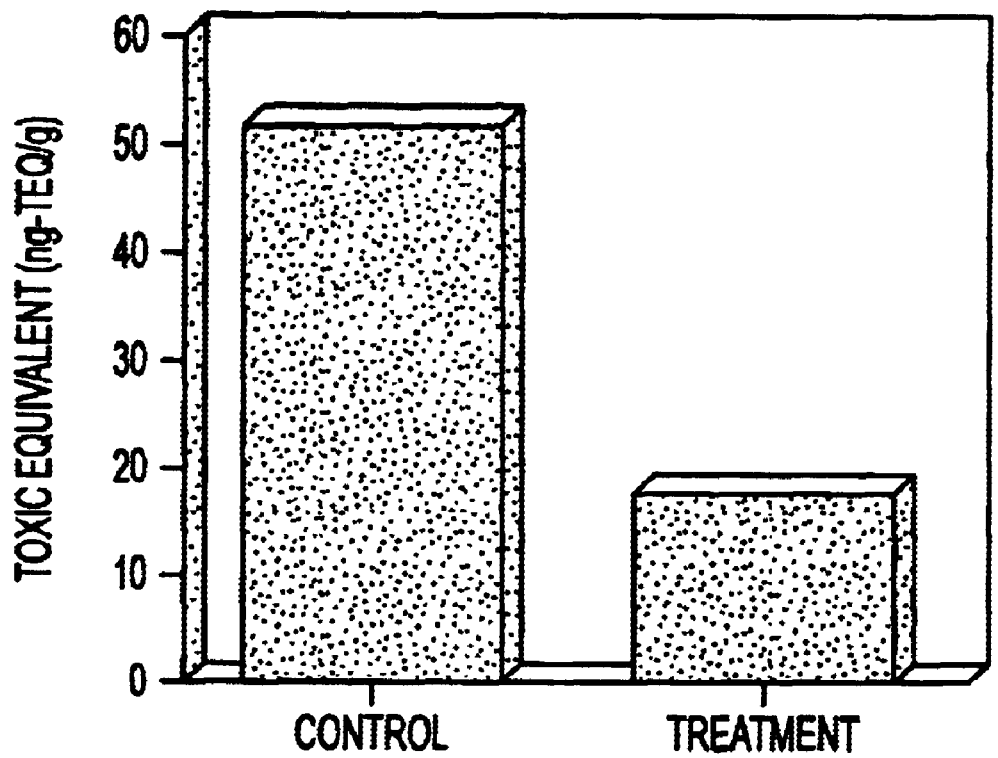
FIG. 3 shows a graph indicating the decrease in the toxic equivalent of total dioxins in incineration ash in a liquid culture system with white rot fungus MZ-340.
Figure 4A:
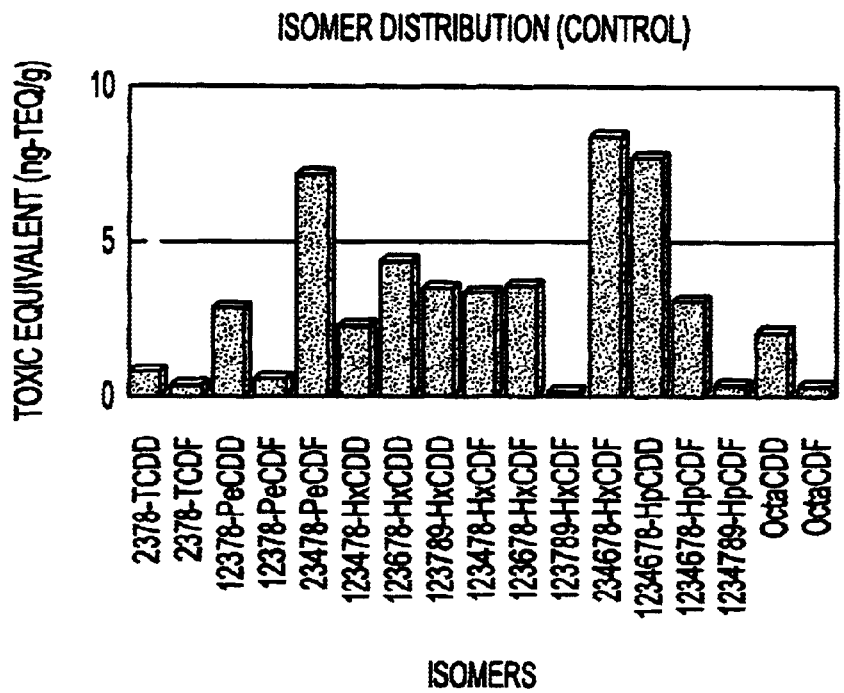
FIG. 4 shows a graph indicating the decreases in the toxic equivalent of dioxins in incineration ash in a liquid phase system with white rot fungus.
Figure 4B:
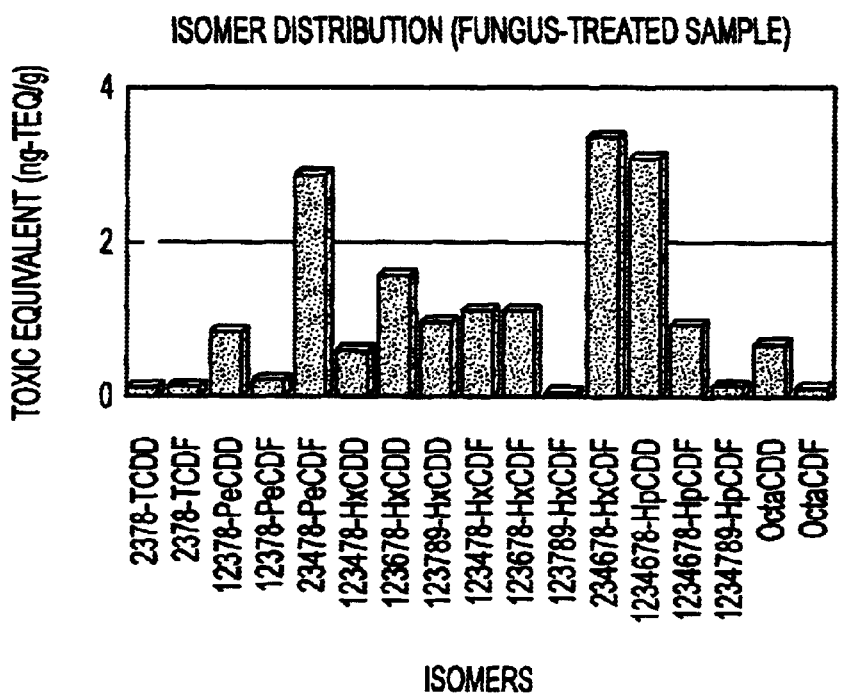
Figure 5A:
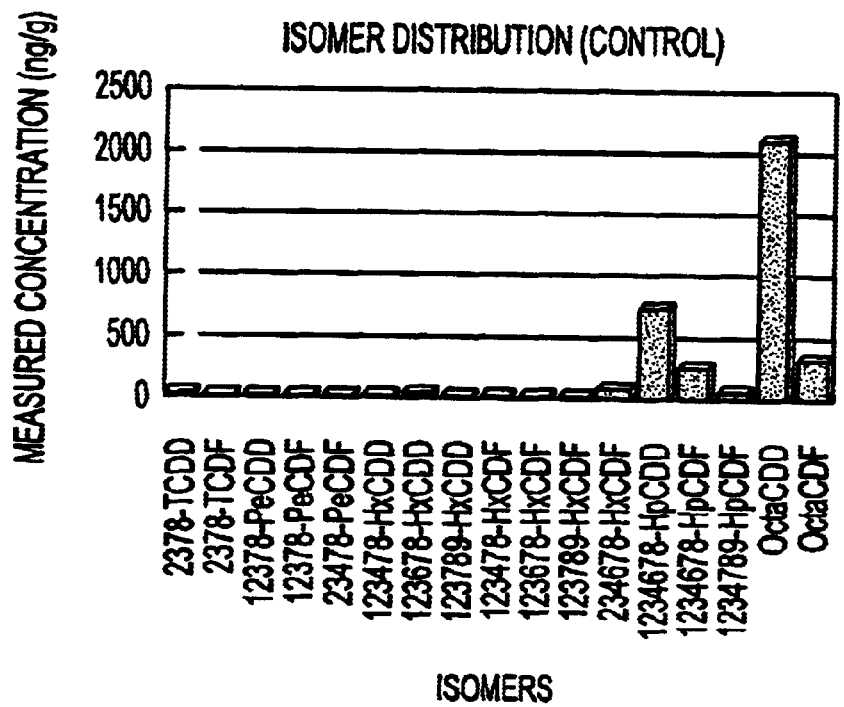
FIG. 5 shows a graph indicating the decreases in dioxin concentration in incineration ash in the liquid phase system with white rot fungus.
Figure 5B:
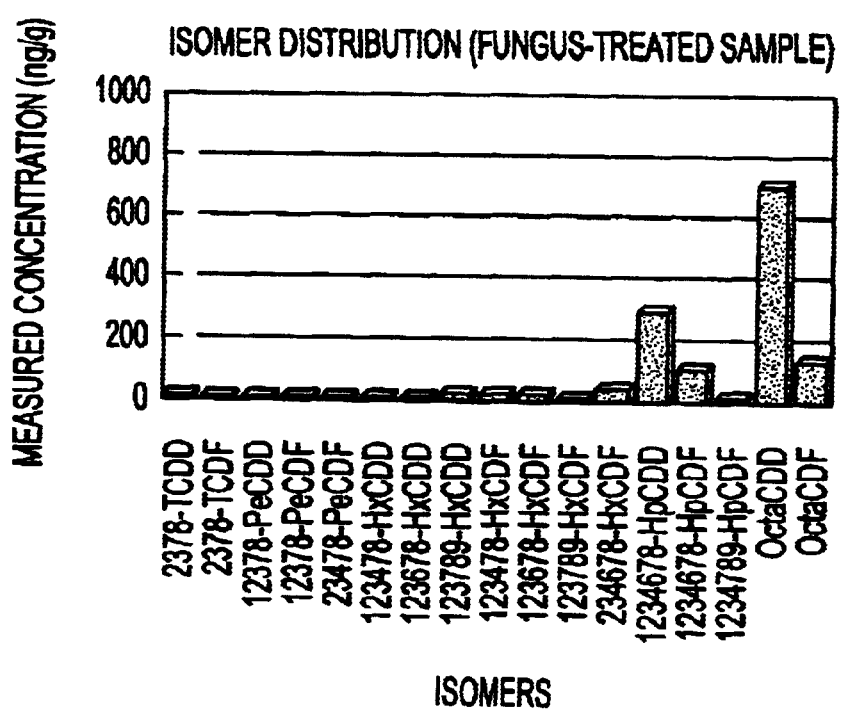
Figure 6:
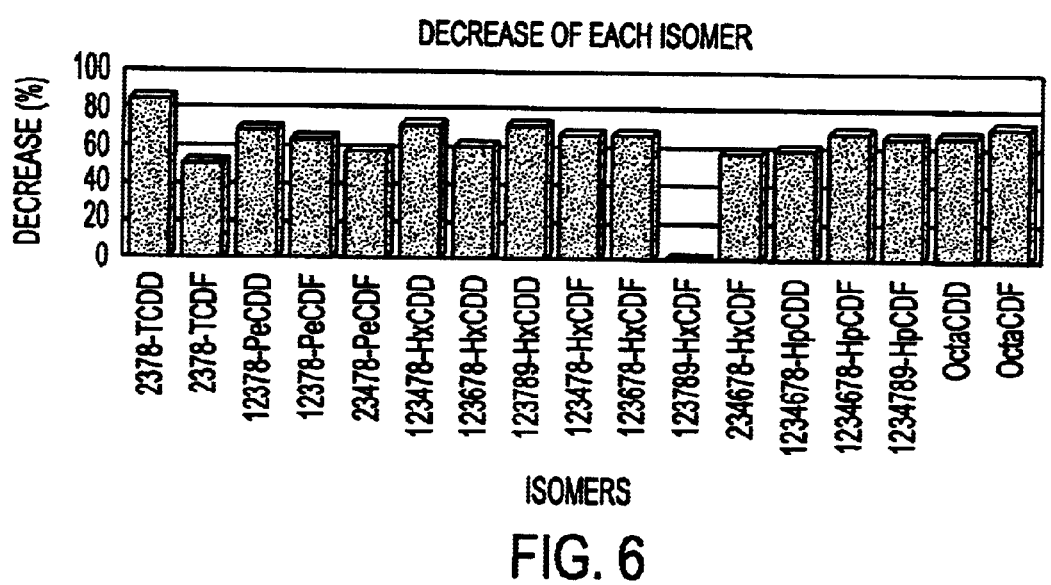
FIG. 6 shows a graph indicating the reducing rate of dioxins in incineration ash in the liquid phase system with white rot fungus.

While the toxic equivalent of total dioxins in fly ash was 52.02 ng-TEQ/g in the control, the toxic equivalent decreased to 18.63 ng-TEQ/g (decreased by 64.18%) in the sample cultured two weeks with the MZ-340 strain (FIG. 3). The quantities of each of the dioxin isomers from fly ash were assayed in controls and treated samples, and the result is shown in FIGS. 4, 5, and 6. It was observed that each isomer was decomposed by MZ-340 and there were no marked differences in the degree of decomposition between the isomers. This suggests that the decomposition by MZ-340 strain has no significant difference in substrate specificity to chloro-substituted compounds.

EXAMPLE 7

Decomposition of Dioxin Contained in Incineration Ash by Using a Solid Phase Culture System The white rot fungus MZ-340 strain exhibits a high 2,7-DCDD decomposing activity and hyphae extension in fly ash containing a high concentration of metal. Thus, the direct decomposition of dioxins was attempted in fly ash.

Bran was added to a mixed medium of white birch chips and beech wood meal. The moisture content of the medium was adjusted to 60%. The medium was placed in a polyethylene bag for Shiitake mushroom bed cultivation, and the MZ-340 strain was inoculated thereto. The culture was continued at 20° C. for 3 to 4 weeks.

Thus, MZ-340 strain was cultured in a large scale by using a wood-based material. Active hyphae extension was observed under conditions usually used for bed cultivation of edible mushrooms. Thus, a fungal culture medium in which the hyphae were sufficiently spread was obtained by about a 3-week culture.

After the hyphae were sufficiently extended in the medium, the fungal culture medium was taken out of the polyethylene bag and disassembled into small pieces. The small pieces of fungal culture medium was mixed well with fly ash. The moisture content was adjusted to 65%. The mixed sample was placed in a plastic container (44 cm×73 cm×40 cm) to a height of about 15 cm and then allowed to stand still at about 25° C. in a culture room for a required period of time. The assay was also carried out by altering the mixing ratio between fungal culture medium and fly ash, as well as by using pre-mixed fly ash and wood meal. A sample of a mixture of fungal culture medium and fly ash taken immediately after mixing, and a sample of a mixture of autoclaved fungal culture medium and fly ash taken after allowing to stand still for a desired period of time, were used as controls. The assay for dioxin concentration in samples was carried out by commonly used methods.

Assay result for dioxins in fly ash used in the experiment is shown in Table 2. The toxic equivalent was 62.2 ng/g.

Figure 7B:
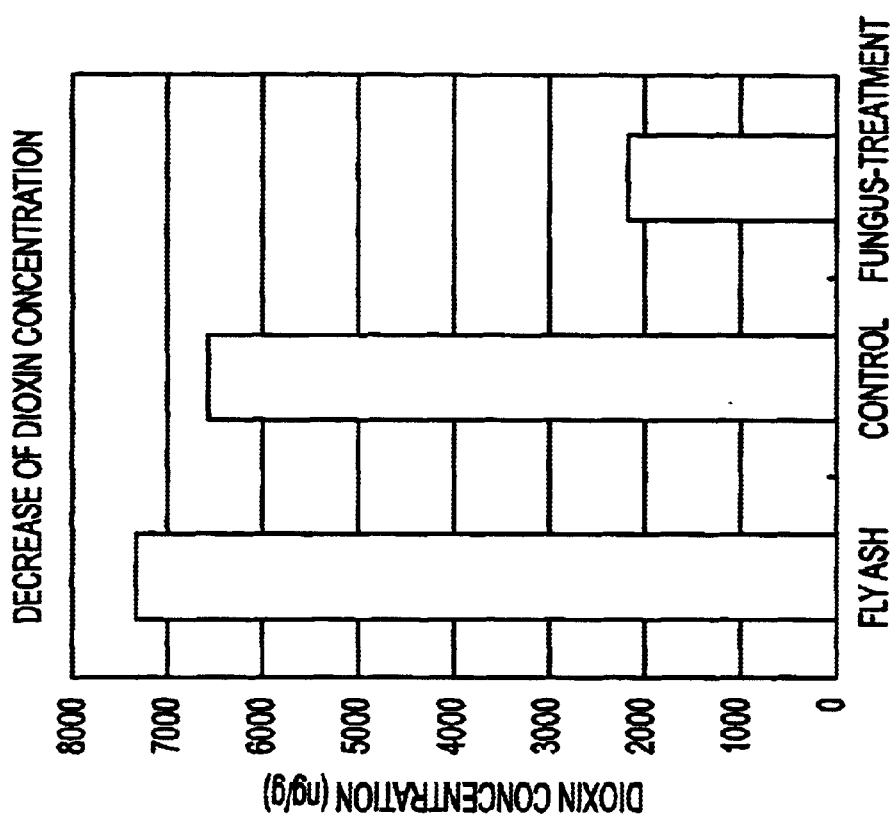
FIG. 7 shows graphs indicating the decreases in the toxic equivalent (A) and in the concentration of dioxins (B) in incineration ash in a solid phase with white rot fungus.
Figure 7A:
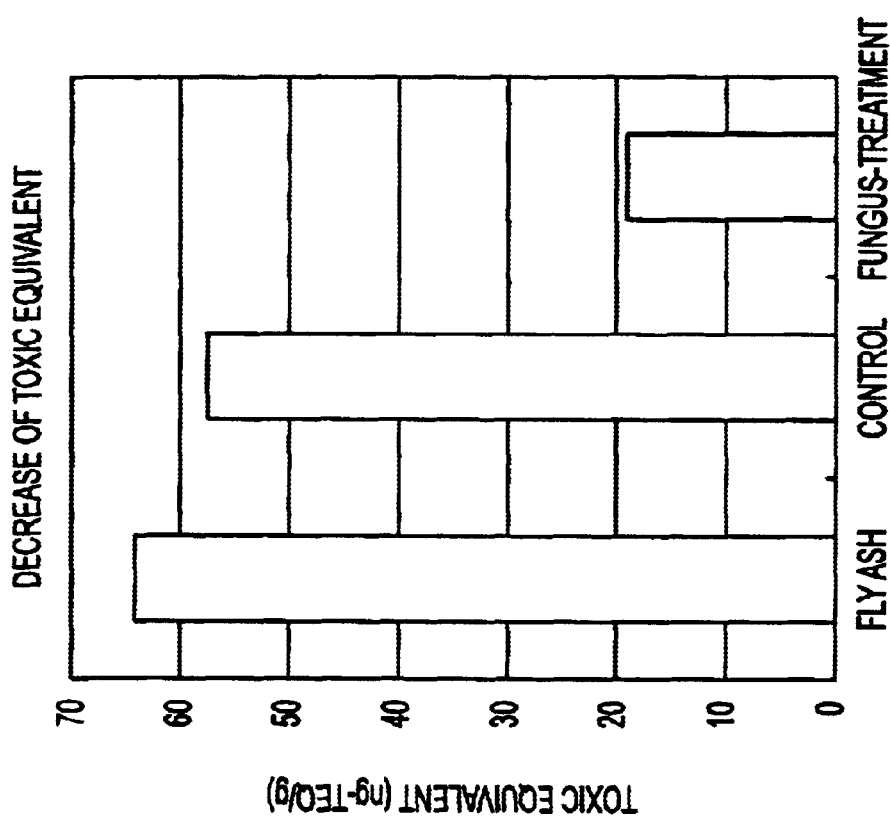

The mixing ratio between fly ash and fungal culture medium was altered from 1:1 to 1:16. When the ratio of fly ash:fungal culture medium was 1:1, hyphae extension was not observed. However, as the ratio of fungal culture medium:fly ash increased, hyphae extension and the enwrapping of fly ash by hyphae were observed. When wood meal was pre-mixed with fly ash, a relatively uniform propagation of hyphae was observed. After being treated for a required period of time, samples were collected from several places and their dioxin contents were assayed according to a commonly used method. An example of experimental result is shown in Table 2, in which fungal culture medium, fly ash, and wood meal were mixed together at a ratio of 4:1:1 and the treatment was continued for 30 days. As compared with an autoclaved control, the sample showed a significant decrease in dioxin content, and the toxic equivalent decreased by 67%. There were no significant differences in the rate of decrease among the isomers. A result obtained in a similar experiment is also shown in FIG. 7.

TABLE 2

Dioxin concentrations in fly ash

| | Fly ash before treatment | | Control | | Fly ash after treatment | |
|---|---|---|---|---|---|---|
| | ng/g | TEQ ng/g | ng/g | TEQ ng/g | ng/g | TEQ ng/g |
| 2378-TCDD | 0.72 | 0.72 | 0 | 0 | 0 | 0 |
| T4CDDs | 15.15 | 0 | 0 | 0 | 0.53 | 0 |
| 12378-PeCDDs | 5.94 | 2.97 | 4.02 | 2.01 | 1.21 | 0.61 |
| P5CDD | 94.67 | 0 | 29.46 | 0 | 14.85 | 0 |
| 123478-HxCDD | 21.23 | 2.12 | 14.38 | 1.44 | 3.38 | 0.34 |
| 123678-HxCDD | 50.62 | 5.06 | 37.01 | 3.70 | 9.13 | 0.91 |
| 123789-HxCDD | 38.09 | 3.81 | 28.24 | 2.82 | 6.79 | 0.68 |
| H6CDD | 518.36 | 0 | 427.93 | 0 | 98.24 | 0 |
| 1234678-HpCDD | 1023.42 | 10.23 | 788.18 | 7.88 | 278.98 | 2.79 |
| H7CDD | 1760.51 | 0 | 1281.81 | 0 | 461.24 | 0 |
| OctaCDD | 2454.55 | 2.45 | 1799.21 | 1.80 | 631.52 | 0.63 |
| Total PCDDs | 4843.24 | 27.38 | 3538.40 | 19.66 | 1206.38 | 5.96 |
| 2378-TCDF | 3.92 | 0.39 | 3.90 | 0.39 | 0.70 | 0.07 |
| T4CDF | 129.25 | 0 | 56.78 | 0 | 21.21 | 0 |
| 12378-PeCDF | 11.94 | 0.60 | 8.47 | 0.42 | 2.26 | 0.11 |
| 23478-PeCDF | 15.86 | 7.93 | 10.93 | 5.46 | 2.68 | 1.34 |
| P5CDF | 223.97 | 0 | 122.78 | 0 | 33.74 | 0 |
| 123478-HxCDF | 44.79 | 4.48 | 26.31 | 2.63 | 7.52 | 0.75 |
| 123678-HxCDF | 45.02 | 4.50 | 35.92 | 3.59 | 9.25 | 0.92 |
| 123789-HxCDF | 6.88 | 0.69 | 0 | 0 | 0 | 0 |
| 234678-HxCDF | 115.25 | 11.52 | 81.46 | 8.15 | 20.07 | 2.01 |
| H6CDF | 609.38 | 0 | 392.02 | 0 | 102.59 | 0 |
| 1234678-HpCDF | 375.48 | 3.75 | 268.95 | 2.69 | 73.51 | 0.74 |
| 1234789-HpCDF | 58.45 | 0.58 | 26.37 | 0.26 | 7.70 | 0.08 |
| H7CDF | 713.14 | 0 | 529.06 | 0 | 122.38 | 0 |
| OctaCDF | 423.04 | 0.42 | 325.95 | 0.33 | 84.16 | 0.08 |
| Total PCDFs | 2098.78 | 34.87 | 1426.54 | 23.93 | 364.08 | 6.10 |
| Total (PCDDs + PCDFs) | 6942.02 | 62.25 | 4964.94 | 43.58 | 1570.46 | 12.06 |
| Ignition Loss (%) | | 7.2 | | 24.4 | | 37.1 |

EXAMPLE 8

Phylogenetic Analysis of the White Rot Fungus MZ-340 Strain

The strain MZ-340 is a white rot fungus but its precise biological origin remains unclear. Therefore, the 18S rDNA nucleotide sequence, which encodes 18S ribosomal RNA of this fungal strain was determined. The 18S rRNA is highly conserved in whole eukaryotic organisms. The nucleotide sequence was compared with those from other fungi related to MZ-340 to clarify the taxonomical relation and identity.

First, MZ-340 strain was cultured. Regardless of the type of culture method, only fungal bodies or hyphae can be collected from an agar culture, liquid culture, a fruit body grown on a material, and such. Some agar can be contaminated when the fungus is collected from the agar culture. The hypha can be stored after drying by freeze-drying, air-drying, and such, or stored as a frozen sample. For DNA extraction, mycelia were grown at room temperature or 30° C. on potato dextrose agar or 2% malt extract agar plate. Genomic DNA was extracted from the fungus by the CTAB method. About 150 mg of living hyphae or about 20 to 50 mg of dried hyphae were frozen in liquid nitrogen. The fungal bodies were crushed into fine powder by a mortar and pestle. One milliliter of CTAB II buffer [0.1 MTris-HCl, 2% (W/V) CTAB, 0.1% (V/V) β-mercaptoethanol, 1.4 M NaCl, 20 mM EDTA, pH 9.0] preheated at 60° C. was added to the mortar, which had also been preheated. The fungal bodies were further crushed by using a pestle which had also been preheated. The fungal suspension (600 µl) was recovered and added to a 1.5-ml or 2.0-ml eppendorf tube. The suspension was incubated at 60° C. for 30 minutes.

An equal volume of chloroform was added to the suspension and the mixture was rotated (by inversion) for 10 minutes. After this treatment, the mixture was centrifuged at 12000 rpm (10000×g) for 5 minutes and the upper layer (aqueous layer) was recovered. This treatment was repeated 3 times.

Sodium acetate (3 M, pH 5.2, 1/10 volume) was added to the recovered aqueous layer, and further, a 0.6 volume of isopropanol or a 2.5 volume or more of ethanol was added thereto. The combined solution was mixed well by using a vortex mixer, and then centrifuged at 12000 rpm (10000×g) for 5 minutes. The supernatant was completely discarded, and the pellet was recovered. The pellet was washed well with 70% ethanol for desalting. The sample was centrifuged again in the same manner. The pellet was recovered and air-dried. The pellet of genomic DNA was dissolved in TE buffer (10 mM Tris-HCl, 1 mM EDTA; pH 8.0).

The genomic DNA extracted from the fungal bodies was adjusted to a concentration of 50 ng/µl and used at a final concentration of 5ng/µl in the PCR experiment. PCR was performed with EXtaq polymerase (TaKaRa) and primers designed for the 18S rRNA sequence. The primers were prepared by referring to a report by Dams et al. (Dams, E. et al., Nucleic Acids Res., 1988, 16 (Sup.), r87–173). The primers used are as follows:

EukNS20F: TGTAGTCATATGCTTGTCTCAA (SEQ ID NO: 1)

EukNS600R: ATACGCTATTGGAGCTGGAA (SEQ ID NO: 2)

EukNS581F: TCCCAGCTCCAATAGCGTAT (SEQ ID NO: 3)

EukNS1165R: CCTGGTGGTGCCCTTCC (SEQ ID NO: 4)

-continued

EukNS1149F: GGAAGGGCACCACCAGG (SEQ ID NO: 5)

EukNS1750R: TCCTCTAAATGACCAAGTTTG (SEQ ID NO: 6)

The PCR reaction was carried out in 100 µl reaction solution at 94° C. for 90 sec; 32 cycles of 94° C. for 30 sec, 55° C. for 30 sec, and 72° C. for 2 min; and at 72° C. for 5 min. After the end of the reaction, the amplified fragments were purified by using a QIAquick™ PCR Purification Kit (QIAGEN). The sample was sequenced in a genetic analyzer ABI377 (PerkinElmer (PE)) by the four-color dye terminator method. The diluent used for the enzyme solution used in the sequencing reaction was halfBD (GENPACK) or 5X sequencing buffer (PE). A set of partial sequence data were assembled together by using a software for sequencing analysis "GENETYX-MAC 9.0". The sequence was determined from both sense and antisense strands. The identified 18S rDNA sequence of MZ-340 strain is shown in SEQ ID NO: 7.

The sequence determined was aligned with the sequences deposited in "GenBank" (http://www2.ncbi.nlm.nih.gov/genbank/query_form.html) or other sequence data by multiple-alignment procedures. The multiple-alignment was made by using softwares "SeqPup" and "Clustal X." The alignment data within an overlapping region conserved in all the genes were used for the phylogenetic analysis. The software "SeqPup" was available at http://iubio.bio.indiana.edu/soft/molbio/seqpup; "Clustal X" at ftp://ftp.ebi.ac.uk/pub/software/mac/clustalw/clustalx/.

Phylogenetic analysis using the alignment obtained was performed by a software for phylogenetic analysis, "Phylip package 3.572." A Kimura 2-parameter distance matrix was made by using the program "DNADIST." Then, phylogenetic analysis was performed according to the Neighborhood-Joining (NJ) method by using the program "NEIGHBOR." Bootstrap analysis was carried out with 100 data sets selected at random by using the program "SEQ-BOOT." Subsequently, based on the obtained data, a phylogenetic tree was constructed by using the program "Tree-View" (Trends in Glycoscience and Glycotechnology, 1999 May, 11(59), (199–127). The software package "Phylip package3.572" was obtained from ftp://evolution.genetics.washington.edu/phylip.html; "TreeView" was obtained from http://taxonomy.zoology.gla.ac.uk/rod/treeview.html.

Figure 8:
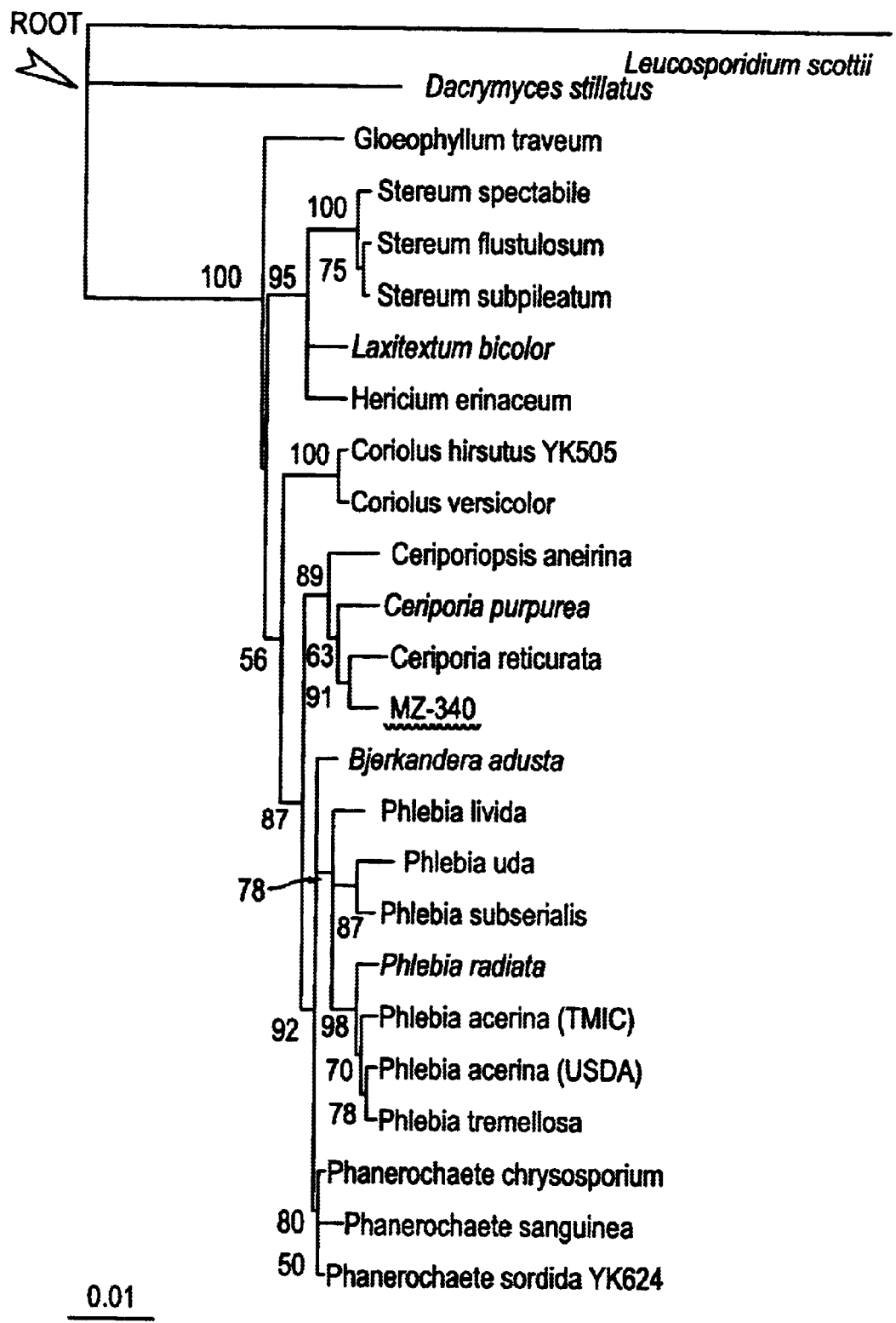
FIG. 8 shows a phylogenetic tree constructed by the Neighborhood-Joining method based on 18S rDNA nucleotide sequences from white rot fungus MZ-340 and other fungi. Names that have been previously reported are indicated in italics. Numerals at each branch indicate bootstrap values obtained by analyzing 100 data sets selected at random.

The analytical result obtained by the Neighborhood-Joining method is shown in FIG. 8. In this figure, previously reported data are indicated in italics. From the result of phylogenetic analysis, MZ-340 strain is presumed to belong to the family Corticiaceae. Each of the three genuses, the genus Ceriporia, the genus Phanerochaete, and the genus Phlebia, which appear to be closely related to the MZ-340 strain, forms a single phylogenetic group. The analysis conducted assigned the MZ-340 strain to a phylogenetic group of the genus Ceripolia. The bootstrap value showed a high level of reliability for the separation of the three phylogenetic groups. Judging from the above result, MZ-340 strain may be a fungus belonging to the genus Ceriporia. Species assignment is still obscure but there is a possibility that MZ-340 strain may be *Ceriporia alachuana* according to the morphological observations of the fruit body.

INDUSTRIAL APPLICABILITY

The present invention provides the white rot fungus MZ-340 strain capable of decomposing dioxins. The strain enables effective and efficient decomposition of dioxins.

Further, white rot fungus MZ-340 can be cultured in the Kirk liquid medium (HCLN) or PDB medium, which is advantageous cause it enables easy and efficient acquisition of the white rot fungus MZ-340 capable of decomposing dioxins.

Moreover, the present invention provides amethod of decomposing dioxins using the white rot fungus MZ-340, thus having the advantage of being capable of effectively and efficiently decomposing dioxins.

In addition, dioxins can be decomposed by using the crude extracellular enzyme from the white rot fungus in the inventive method of decomposing dioxins. Thus dioxins, particularly various dioxins including polychlorinated dibenzo-p-dioxin and polychlorinated dibenzofuran, can be decomposed more effectively and efficiently.

The present invention also provides a method for decomposing dioxins in incineration ash by using the white rot fungus. The method is simple and can be conducted without any special facilities. Thus dioxins in incineration ash can be conveniently decomposed. The method of the present invention provides a breakthrough for solving environmental problems associated with dioxins.

What is claimed is:

1. A method for decomposing a dioxin in incineration ash, the method comprising incubating a mixture of:
    (a) a white rot fungus specified by the accession number FERM BP-6864, a crude extracellular enzyme from the white rot fungus, a medium containing the white rot fungus, or a culture medium of the white rot fungus that does not substantially contain fungal bodies of the white rot fungus, and
    (b) incineration ash.

2. The method of claim 1, wherein the mixture is incubated in a liquid phase.

3. The method of claim 2, wherein the mixture is incubated in the Kirk liquid medium (HCLN).

4. The method of claim 1, wherein the mixture is incubated in a solid phase.

5. The method of claim 4, wherein the mixture is incubated in the presence of a wood-based material.

6. A method for decomposing a dioxin, the method comprising contacting a dioxin with a white rot fungus specified by the accession number FERM BP-6864, a crude extracellular enzyme from the white rot fungus, a medium containing the white rot fungus, or a culture medium of the white rot fungus that does not substantially contain fungal bodies of the white rot fungus.

7. The method of claim 6, wherein the dioxin is polychlorinated dibenzo-p-dioxin or polychlorinated dibenzofuran.

* * * * *